United States Patent [19]

Waxman et al.

[11] 4,060,418

[45] Nov. 29, 1977

[54] PHENOXY CARBONYL DERIVATIVES OF A PARAPHENYLENEDIAMINE COLOR DEVELOPER AND THEIR USE IN AN IMAGE-RECEIVING SHEET FOR COLOR DIFFUSION TRANSFER

[75] Inventors: Burton H. Waxman, Endwell; Michael C. Mourning, Vestal, both of N.Y.

[73] Assignee: GAF Corporation, New York, N.Y.

[21] Appl. No.: 657,855

[22] Filed: Feb. 13, 1976

[51] Int. Cl.$^2$ .......................... G03C 7/00; G03C 5/54; G03C 1/40; C07C 79/46

[52] U.S. Cl. .......................................... 96/29 D; 96/3; 96/55; 96/77; 96/100 R; 428/411; 560/32

[58] Field of Search .................. 96/3, 29 D, 77, 66 R, 96/55, 96, 100, 91 R; 260/471 C; 428/411

[56] References Cited

U.S. PATENT DOCUMENTS

| | | | |
|---|---|---|---|
| 2,026,618 | 7/1934 | Etzelmiller | 260/471 C |
| 2,026,619 | 7/1934 | Etzelmiller | 260/471 C |
| 2,559,643 | 7/1951 | Land | 96/29 D |
| 2,774,668 | 12/1956 | Rogers | 96/29 D |
| 3,291,609 | 12/1966 | Porter | 96/95 |
| 3,301,772 | 1/1967 | Viro | 96/29 D |
| 3,359,104 | 12/1967 | Viro | 96/29 D |
| 3,584,000 | 6/1961 | Hobart et al. | 260/471 C |
| 3,728,116 | 4/1973 | Waxman et al. | 96/29 D |

OTHER PUBLICATIONS

"Alkali-Releasable Incorporated Developer Derivatives," *Research Disclosures,* No. 9423, 2/1972.

*Primary Examiner*—David Klein
*Assistant Examiner*—Richard L. Schilling
*Attorney, Agent, or Firm*—Walter C. Kehm; Edward G. Comrie

[57] ABSTRACT

Compounds of the formula:

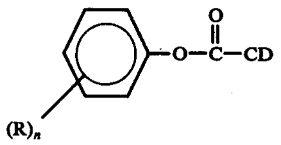

wherein R is halogen or trifluoromethyl, *n* is 0 to 5, and CD is the residue of a paraphenylenediamine color developer having a primary amino group available for oxidative coupling, the phenoxycarbonyl group being attached to the primary nitrogen atom of the paraphenylenediamine color developer, are used in a receiving sheet of a diffusion transfer photographic element for coupling with a color former to form a stable dye.

15 Claims, No Drawings

PHENOXY CARBONYL DERIVATIVES OF A PARAPHENYLENEDIAMINE COLOR DEVELOPER AND THEIR USE IN AN IMAGE-RECEIVING SHEET FOR COLOR DIFFUSION TRANSFER

The present invention relates to new paraphenylenediamine derivatives which are useful in forming indoaniline or azomethine dyes by reaction with color formers, and more particularly to a receiving sheet for a diffusion transfer photographic element containing the new paraphenylenediamine derivatives.

In diffusion transfer photography, formation of a dye image in a receiving sheet may be effected by diffusion of a color former from the negative portion of a film pack to the receiving sheet of the film pack. The diffusion is normally a function of imagewise non-exoposed areas of the film pack, and a positive dye image is formed by coupling of the transferred color former with oxidized paraphenylenediamine to form a stable, non-diffusing dye. Many different systems have been proposed for supplying oxidized paraphenylenediamine color developer to the receiving sheet, such as incorporating a paraphenylene diamine color developer or precursor thereof in the film pack or the processing solution, but these proposals all suffer from the known disadvantage of paraphenylenediamine, namely its lack of stability to aerial oxidation and other forms of environmental degradation, its tendency to fog a silver halide emulsion, its allergenic properties, and the like.

There is thus a need for a derivative of a paraphenylenediamine color developer that can be incorporated into a receiving sheet of a diffusion transfer film unit and that is available for coupling with a color former to form a stable dye, without liberation of paraphenylenediamine.

It is thus an object of the invention to provide a paraphenylenediamine derivative that can be incorporated into a photographic element.

It is another object of the present invention to provide such a paraphenylenediamine derivative that has the required stability to resist environmental degradation.

These and other objects of the invention are provided by the present invention, which resides in a derivative of paraphenylenediamine of the formula:

A — CD (I)

where A is a phenoxycarbonyl group of the formula:

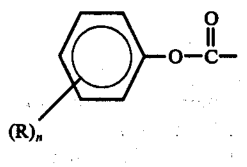
(Ia)

where R is halogen or trifluoromethyl, *n* is 0 to 5, and CD is the residue of a paraphenylenediamine color developer having a primary amino group available for oxidative coupling, said phenoxycarbonyl group being attached to the primary nitrogen atom of said paraphenylenediamine color developer for use in the receiving sheet of a diffusion transfer color photographic element.

The present invention also provides a receiving sheet for a diffusion transfer color photographic element having incorporated therein the paraphenylenediamine derivative of the invention.

The present invention is based on the fact that when the paraphenylenediamine derivatives (I) are treated with a strong oxidizing agent, the phenoxycarbonyl group (I*a*) will be split off, and the oxidized form of the color developer moiety, CD, will couple with a color former in an alkaline medium to form an indoaniline or azomethine dye. Both the derivative (I) and the oxidized form thereof are free from the disadvantages of known paraphenylenediamine color developers or precursors thereof. In particular, the derivative (I) possesses excellent resistance to aerial oxidation and is suitable for incorporation into the receiving sheet.

The paraphenylenediamine derivatives (I) are based on replacing a hydrogen atom of a primary amino group of a paraphenylenediamine color developer with the phenoxycarbonyl group (I*a*) in which the phenoxy is either unsubstituted or substituted by 1 to 5, preferably 1 to 3, halogen or trifluoromethyl groups. This structure enables the derivative (I) to resist splitting off of the phenoxycarbonyl group (I*a*) during coating and storage in the film unit, and to split off the phenoxycarbonyl group (I*a*) and form an oxidized paraphenylenediamine color developer alkaline media when treated with a strong oxidizing agent. When R is halogen, the halogen is preferably chlorine or bromine.

Since it is the oxidized paraphenylenediamine color developer moiety which undergoes oxidative color coupling, this moiety may be provided by any paraphenylenediamine color developer. Paraphenylenediamine color developers are well known, and an extensive list of suitable paraphenylenediamine color developers for use as the moiety CD is presented in J.Am.Chem.-Soc., 73, pages 3100–3125 (1951) in the article by Bent et al. In particular, the moiety CD may represent:

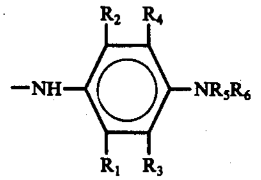

where (A)

$R_1$ and $R_2$ are independently hydrogen, halogen, an aliphatic group or an aromatic group;

$R_3$ and $R_4$ are independently hydrogen or COOH, and $R_5$ and $R_6$ are independently hydrogen, an aliphatic group or an aromatic group; or (B)

$R_1$, $R_2$, $R_3$ and $R_6$ are as defined in (A) and $R_4$ and $R_5$ together represent the necessary ring members to form a heterocyclic ring with the nitrogen atom to which $R_5$ is attached being the sole heteroatom or there being a second heteroatom selected from nitrogen, oxygen and sulfur; or (C)

$R_1$, $R_2$, $R_3$ and $R_4$ are as defined in (A) and $R_5$ and $R_6$ together represent the necessary ring members to form a heterocyclic ring with the nitrogen atom to which they are attached being the sole heteroatom or there being a second heteroatom selected from nitrogen, oxygen and sulfur.

In a preferred embodiment of the invention, $R_1$ and $R_2$ are independently hydrogen, halogen, an aliphatic group or an aromatic group;

$R_3$ and $R_4$ are independently hydrogen or COOH; and $R_5$ and $R_6$ are independently hydrogen, an aliphatic group or an aromatic group; or $R_4$ and $R_5$ together with the nitrogen atom to which $R_5$ is attached form a 5- to 7-membered heterocyclic ring with said nitrogen atom being the sole heteroatom; or $R_5$ and $R_6$ together with the nitrogen atom to which they are attached form a 5- to 7-membered heterocyclic ring with said nitrogen atom being the sole heteroatom or there being a second heteroatom selected from nitrogen, oxygen and sulfur.

In these embodiments, when $R_1$ or $R_2$ is aromatic, it is preferably phenyl or phenoxy, and when $R_5$ or $R_6$ is aromatic, it is preferably phenyl. Useful derivatives (I) are provided when $R_1$ and $R_2$ are independently hydrogen, straight or branched chain alkyl or alkoxy of 1 to 18 carbon atoms, most preferably lower alkyl or lower alkoxy;

$R_3$ and $R_4$ are independently hydrogen or COOH; and $R_5$ and $R_6$ are independently straight or branched chain alkyl of 1 to 18 carbon atoms, most preferably lower alkyl.

The terms "lower alkyl" and "lower alkoxy" as used herein denote a chain of from 1 to 6 carbon atoms.

The term "aliphatic group" may be any of the aliphatic groups illustrated in the above-mentioned J.Am.-Chem.Soc. article. Accordingly, it is to be understood that the term "aliphatic group" is exemplified by, but not limited to, alkyl, alkoxy, alkylamido, or alkyl substituted by lower alkoxy, sulfonamido, alkylsulfonamido, carbamyl, hydroxy or amino. As examples of saturated or unsaturated heterocyclic rings containing nitrogen as the sole heteroatom or containing sulfur, oxygen or nitrogen as the second heteroatom, which are formed when $R_4$ and $R_5$ or $R_5$ and $R_6$ are joined together, there may be mentioned pyrrolidino, piperidino, piperazino, morpholino, hexahydroazepino, dihydroindol and tetrahydroquinoline.

Useful paraphenylenediamine derivatives (I) include:

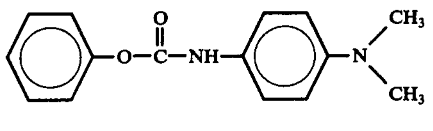

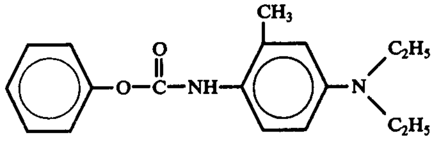

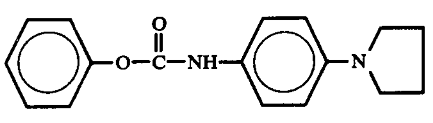

-continued

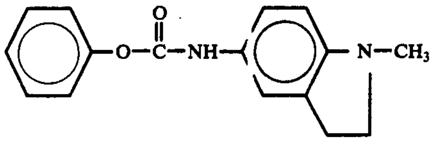

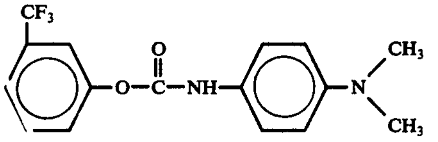

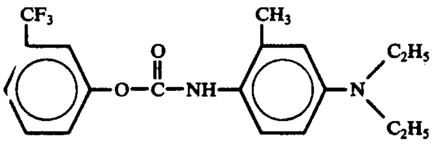

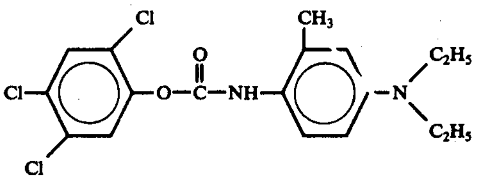

The paraphenylenediamine derivatives (I) are readily prepared by reaction of the chloroformate,

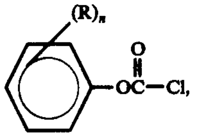

(II)

with the paraphenylenediamine color developer to form a urethane linkage. This can be illustrated as follows:

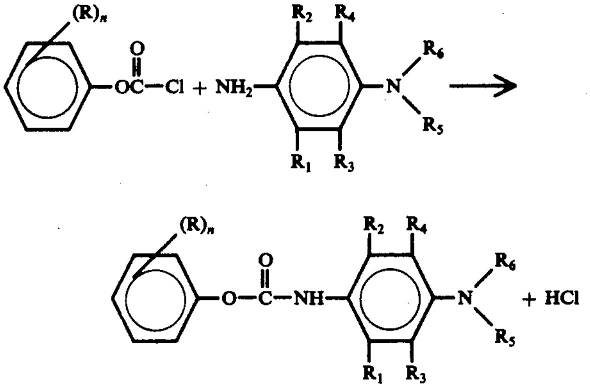

where R, *n* and $R_1$-$R_6$ are as defined above. Phenyl chloroformate is available commercially. Halophenyl chloroformates are either available commercially or can be prepared by reaction of the desired halophenol and phosgene (J.Chem.Soc., 2461 (1965).

The reaction between the chloroformate (II) and the color developer to form the derivative (I) is based on the procedure of Carpino et al, J.Am.Chem.Soc., 92, page 5748 (1970). In this reaction, either the color developer or the chloroformate (II) can be used in excess of the stoichiometric amounts, and the reactants are brought together in an alkaline aqueous reaction medium, which may contain an organic solvent, such as dioxane. The reaction proceeds rapidly with liberation of heat, and the reaction medium is desirably cooled during the reaction period. The paraphenylenediamine derivative (I) is insoluble in the liquid reaction medium and is recovered therefrom by filtration and working up of the wet solid by conventional techniques.

The paraphenylenediamine derivatives of the invention are used in diffusion transfer photography where a color former is caused to diffuse to a receiving sheet for conversion to a stable dye image, either with or without delayed diffusion. See, e.g. U.S. Pat. Nos. 2,774,668, 3,301,772 and 3,359,104. In such systems, the photographic element includes a negative unit containing at least one silver halide emulsion sensitized to light of a primary color and a color former that will couple with oxidized color developer in imagewise exposed areas of the photographic element to form a non-diffusible coupled product, the color of which being irrelevant since it plays no part in the image-forming process. In unexposed areas, the color former is free to diffuse to a receiving element or receiving sheet. In imagewise non-exposed areas, the color former diffuses to a receiving sheet or layer of the photographic element, which contains the paraphenylenediamine derivative of the invention. The receiving sheet is then contacted with an alkaline processing solution containing a strong oxidizing agent, which oxidizes the paraphenylenediamine derivative and enables the oxidized product to couple with the color former to form a stable indoaniline or azomethine dye.

The receiving sheet can be kept in contact with the negative unit of the photographic element during treatment of the negative unit with a photographic color developer, in which case the diffusion of the color former to the receiving sheet can occur without further treatment. Alternatively, the receiving sheet can be married to the negative unit after development, and then the diffusion of the color former is initiated. Both alternatives are effected by known techniques. In either case, the treatment of the receiving sheet with the strong oxidizing agent brings about the formation of the positive dye image.

Where the negative film unit contains the incorporated color developer of Waxman et al, U.S. Ser. No. 1,531,399, filed Dec. 10, 1974, which is incorporated herein by reference thereto, and the receiving sheet contains the paraphenylenediamine derivative of the invention, a color diffusion transfer system is provided that totally avoids any paraphenylenediamine stored in an alkaline processing solution. In other systems, where a paraphenylenediamine color developer is used for color development of the negative film unit, the use of the paraphenylenediamine derivative (I) avoids the use of a paraphenylenediamine color developer in the dye formation step.

The receiving sheet or layer is prepared by dispersing or dissolving the paraphenylenediamine derivative (I) into a high boiling, photographically inert oily material, such as high boiling esters, alcohols, oils or mixtures thereof, dispersing the oil/derivative (I) admixture in an aqueous hydrophilic colloid, e.g. gelatin, with the use of an emulsifier, if desired, and then coating the colloid dispersion over a suitable support. Gelatin is a suitable hydrophilic colloid for use in the receiving sheet, as are polyvinylalcohol and the various synthetic gelatin substitutes. The support may be paper, cellulose acetate, polyethylene terephthalate or any other suitable photographic support. An amount of the paraphenylenediamine derivative (I) is used that ensures oxidative coupling with all color former transferred to the receiving sheet, and hence the optimum amount for a given receiving sheet will depend on the system for which it is used.

The strong oxidizing agent may be an alkali metal or ammonium persulfate or perhalide, or any other oxidizing agent that will split the urethane linkage of the paraphenylenediamine derivative (I). Sufficient oxidizing agent should be used to oxidize all of the paraphenylenediamine derivative (I) in the receiving sheet, and the optimum amount can be readily determined empirically. The oxidizing agent can be in the receiving sheet itself, by inclusion in the hydrophilic colloid during the coating, or can be separately applied to the receiving sheet in a processing solution.

Color formers used in diffusion transfer color photography are suitable for use with the paraphenylenediamine derivative (I). For example, the colorless couplers disclosed in Viro U.S. Pat. Nos. 3,301,772, 3,359,104 and 3,728,116, which are incorporated herein by reference thereto, may be used to advantage.

The present invention is illustrated by the following Examples. All parts and proportions referred to herein and in the appended claims are by weight unless otherwise stated.

EXAMPLE 1

Preparation of:

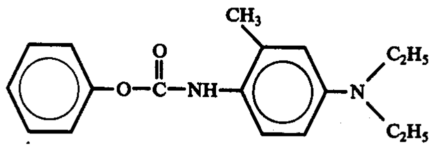

To a solution of 10.6g of sodium carbonate in 100.0 ml water were added 100.0 ml dioxane and 21.4g 4-diethylamino-2-methylaniline hydrochloride. The solution was cooled to 10° C and 15.6g phenylchloroformate was slowly added to the cooled solution, followed by addition of 200.0 of water. The reaction mass was stirred for 15 minutes and then diluted to 1 liter with water. The reaction product was worked up by dissolving the solid in ether followed by drying over sodium sulfate, and evaporation of the ether and recrystallization from a high boiling petroleum ether. The yield was 26g of a product melting at 117°-118° C and having the structure shown above. The carbon hydrogen nitrogen analysis was as follows:

| | Calc. | Found |
|---|---|---|
| C | 72.45 | 72.23; 72.23 |
| H | 7.43 | 7.61; 7.37 |
| N | 9.39 | 9.41; 9.36 |

EXAMPLE 2

Preparation of:

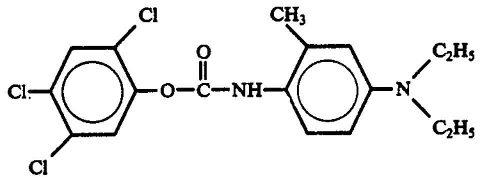

To a solution of 11.0g sodium carbonate and 0.05g sodium sulfite in 100.0 ml water was added 100.0 ml dioxane and 21.6 g 4-diethylamino-2-methylaniline hydrochloride. The solution was cooled to 8° C and 26.0g 2,4,5-trichlorophenylchloroformate in 100 ml of dioxand was added slowly. The resulting solution was stirred at 5° C for 30 minutes and then poured over icewater and filtered. After working up of the solid, including recrystallization from hot petroleum ether, a product having a melting point of 120°-121° C and having the structure shown above was recovered in a yield of 20g. Analysis of the compound was as follows:

| | Calc. | Found |
|---|---|---|
| C | 53.82 | 53.84; 53.71 |
| H | 4.77 | 4.98; 4.87 |
| N | 6.97 | 6.83; 6.74 |
| Cl | 26.48 | 26.46; 26.21 |

EXAMPLE 3

A receiving sheet for a color diffusion transfer photographic system was prepared by coating a mixture of:

The 2,4,5-trichlorophenyl ester of [(4-diethylamino-2-methyl)phenyl] carbamic acid (Ex. 2) 1 g

| | |
|---|---|
| N-butylacetanilide | 4 cc |
| Gelatin | 3 g |
| $H_2O$ | 25 cc |
| Surfactant (ALKANOL B) | 10 cc |
| Formaldehyde (10% solution) | 1 cc |

onto a resin coated paper stock to a thickness of 10 microns.

EXAMPLE 4

Eight grams of cyan color former:

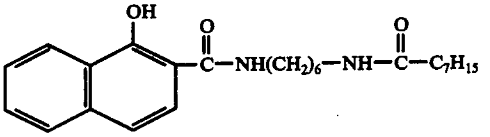

were dissolved in 12 cc of tricresylphosphate and 12 cc of N-butylacetanilide and mixed with 12 g gelatin, 116g $H_2O$, and 40g of ALKANOL B (surfactant). The dispersion was added 1:1 to a (9% by weight silver) silver iodo-bromide emulsion (7.5% gel) and coated on a polyester support to a thickness of 3.0 $\mu$, and hardened with formaldehyde.

The silver halide layer was exposed through a step wedge and processed in the following processing solution:

| | |
|---|---|
| $H_2O$ | 3.2 liters |
| $Na_2SO_3$ | 6.0 g |
| 2-Methyl-4-Diethylamino-Aniline. HCl | 20.0 g |

-continued

| | |
|---|---|
| Benzyl Alcohol | 8.0 cc |
| KOH (45% Solution) | 91.0 cc |
| Boric Acid | 36.0 cc |
| NaCl | 10.0 cc |
| Hydroxylamine Sulfate | 8.0 g |
| PHENIDONE B | 0.5 g |
| pH | 12.5 |

The film strip was processed for 2 minutes in the above developing solution, washed, bleached, fixed and washed, and dried; thus leaving an imagewise distribution of color former. The processed film strip was married to the receiving sheet of Example 3 and the composite unit was treated with a viscous alkaline processing solution (0.1% high M.W. carboxymethyl cellulose adjusted to pH 13.0 with KOH). After a contact time of 1 minute, the film strip was peeled off and the receiving sheet was treated with 1% potassium persulfate solution. A cyan positive image was recorded on the receiving sheet.

EXAMPLE 5

The procedure of Example 4 was repeated using paraphenylene derivatives of the formula:

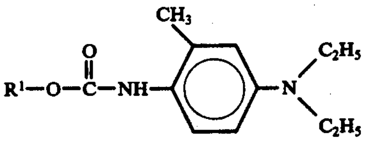

in the receiving sheet in place of the compound of Example 2, with the results reported in the Table below:

| Compound | $R^1$ | Formation of positive cyan image |
|---|---|---|
| 1 | 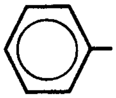 (Ex. 1) | Yes |
| 2 | $C_2H_5$— | No |
| 3 | 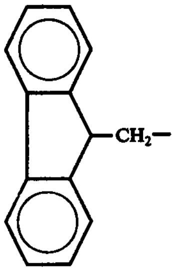 | No |
| 4 | 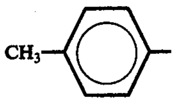 | No |
| 5 | 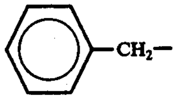 | No |

-continued

| Compound | $R^1$ | Formation of positive cyan image |
|---|---|---|
| 6 | 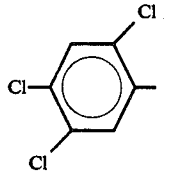 | Yes |

EXAMPLE 6

The procedure of Example 4 was followed to prepare the supported silver halide layer, except that 8.0 grams of 2-methyl-4-(N-methyl-N-tetradecyl)amino-5-carboxy-aniline in addition to the color former were dissolved in the mixture of tricresylphosphate and N-butylacetanilide, according to the aforesaid Waxman et al application Serial No. 531,399. The film unit thus prepared had a color developer incorporated in the silver halide layer. After exposure through a step wedge, the film unit was married to the receiving sheet of Example 3 and simultaneously treated with the following processing solution:

| | |
|---|---|
| $H_2O$ | 400.0 cc |
| $Na_2SO_3$ | 1.5 g |
| KBr | 5.0 g |
| 45% KOH | 20.0 cc |
| Hydroxylamine Sulfate | 1.5 g |
| 1% Carboxymethyl Cellulose | 50.0 cc |
| PHENIDONE B | 0.5 g |
| pH | 13.5 |

After 30 seconds, the receiving sheet was removed from the film unit and treated with a 1% sodium persulfate solution. A cyan positive image was generated.

EXAMPLE 7

The procedure of Example 6 was followed to coat a silver halide layer on a support, except that a red-sensitized silver halide emulsion layer was employed. Over this was coated a separation filter employing colloidal silver (Carey-Lea filter layer) to a thickness of 1.0 μ. A dispersion of 8g of yellow color former:

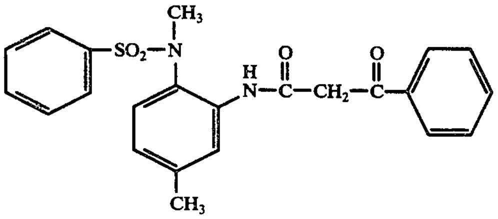

and 8g 2-methyl-4-(N-methyl)-N-tetradecyl)amino-5-carboxyaniline in 20 cc of 2-phenoxypropanol, 20g gelatin, 120 cc $H_2O$, 20 cc of ALKANOL B was formed and then mixed 50:50 with a 9% Ag by weight silver iodobromide emulsion (blue sensitive only), the final emulsion being coated over the separation filter to a thickness of 3.0 μ. The bi-pack was exposed to red and blue light through a step wedge, married to the receiving sheet of Example 3, and processed as in Example 6, with a contact time of 3 minutes. The receiving sheet, after being removed from the film unit, was treated with 1% sodium persulfate solution and yielded positive yellow and cyan images corresponding to red and blue light areas respectively.

What is claimed is:

1. A receiving sheet for a photographic element containing at least one silver halide emulsion layer, which comprises a support carrying a hydrophilic colloid layer containing a compound of the formula:

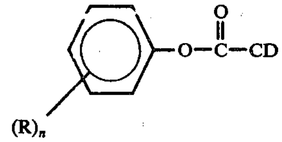

wherein R is halogen or trifluoromethyl, *n* is 0 to 5, and CD is the residue of a paraphenylenediamine color developer having a primary amino group available for oxidative coupling, the phenoxycarbonyl group being attached to the primary nitrogen atom of said paraphenylenediamine color developer.

2. The receiving sheet according to claim 1, wherein the phenoxy group is unsubstituted.

3. The receiving sheet according to claim 1, wherein R is chloro or trifluoromethyl.

4. The receiving sheet according to claim 3, wherein *n* is 1 to 3.

5. The receiving sheet according to claim 1, wherein CD is:

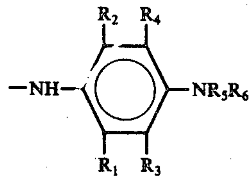

where (A)

$R_1$ and $R_2$ are independently hydrogen, halogen, an aliphatic group or an aromatic group;

$R_3$ and $R_4$ are independently hydrogen or COOH; and $R_5$ and $R_6$ are independently hydrogen, an aliphatic group or an aromatic group; or (B)

$R_1$, $R_2$, $R_3$ and $R_6$ are as defined in (A) and $R_4$ and $R_5$ together represent the necessary ring members to form a heterocyclic ring with the nitrogen atom to which $R_5$ is attached being the sole heteroatom or there being a second heteroatom selected from nitrogen, oxygen and sulfur; or (C)

$R_1$, $R_2$, $R_3$ and $R_4$ are as defined in (A) and $R_5$ and $R_6$ together represent the necessary ring members to form a heterocyclic ring with the nitrogen atom to which they are attached being the sole heteroatom or there being a second heteroatom selected from nitrogen, oxygen and sulfur.

6. The receiving sheet according to claim 5, wherein $R_1$ and $R_2$ are independently hydrogen, halogen, an aliphatic group or an aromatic group;

$R_3$ and $R_4$ are independently hydrogen or COOH; and $R_5$ and $R_6$ are independently hydrogen, an aliphatic group or an aromatic group; or $R_4$ and $R_5$ together with the nitrogen atom to which $R_5$ is attached form a 5- to 7-membered heterocyclic ring with said nitrogen atom being the sole heteroatom; or $R_5$ and $R_6$ together with the nitrogen atom to which they are attached form a 5- to 7-membered heterocyclic ring with said nitrogen atom being the sole heteroatom or there being a second heteroatom selected from nitrogen, oxygen and sulfur.

7. The receiving sheet according to claim 5, wherein $R_1$ and $R_2$ are independently hydrogen, straight or branched chain alkyl or alkoxy of 1 to 18 carbon atoms;

$R_3$ and $R_4$ are independently hydrogen or COOH; and $R_5$ and $R_6$ are independently straight or branched chain alkyl of 1 to 18 carbon atoms.

8. The receiving sheet according to claim 7, wherein $R_1$ and $R_2$ are independently hydrogen, lower alkyl or lower alkoxy, $R_3$ and $R_4$ are independently hydrogen or COOH and $R_5$ and $R_6$ are independently lower alkyl.

9. The receiving sheet according to claim 1, wherein said compound is

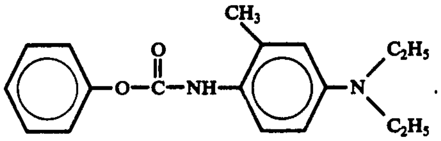

.

10. The receiving sheet according to claim 1, wherein said compound is

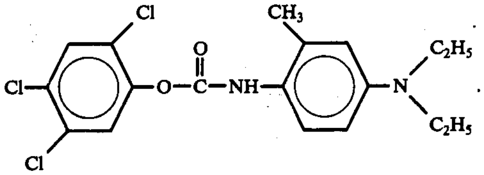

.

11. The receiving sheet according to claim 1, wherein said compound is in admixture with a high boiling, photographically inert oily material, the admixture being dispersed in said colloid.

12. In a process for forming diffusion transfer images in color, in which an imagewise exposed photosensitive diffusion transfer element having at least one photographic silver halide emulsion and a color former associated therewith is developed by contact with an aqueous alkaline processing solution to form an imagewise distribution of diffusible color former in unexposed areas of the silver halide emulsion and at least a portion of said diffusible color former is transferred by imbibition to a superposed image receiving sheet, the improvement wherein the receiving sheet is the receiving sheet of claim 1, the receiving sheet is treated with a strong oxidizing agent to oxidize said compound, and a positive dye image is formed by coupling of the color former transferred to the receiving sheet with said oxidized compound to form an indoaniline or azomethine dye.

13. The process according to claim 12, in which the receiving sheet is in contact with the exposed photosensitive diffusion transfer element during said development and said color former transfer.

14. The process according to claim 13, in which said photosensitive element contains an incorporated color developer.

15. The process according to claim 14, in which, after development, the receiving sheet is removed from the exposed photosensitive diffusion transfer element and treated with said strong oxidizing agent.

* * * * *

Disclaimer 4,060,418.—*Burton H. Waxman,* Endwell and *Michael C. Mourning,* Vestal, N.Y. PHENOXY CARBONYL DERIVATIVES OF A PARAPHENYLENEDIAMINE COLOR DEVELOPER AND THEIR USE IN AN IMAGE-RECEIVING SHEET FOR COLOR DIFFUSION TRANSFER. Patent dated Nov. 29, 1977. Disclaimer filed Sept. 30, 1982, by the assignee, *Eastman Kodak Co.*

Hereby enters this disclaimer to all of the claims of said patent.

[*Official Gazette March 1, 1983.*]